(12) United States Patent
Agar

(10) Patent No.: US 9,455,130 B2
(45) Date of Patent: Sep. 27, 2016

(54) PREPARATION OF TEST PLATES FOR MATRIX ASSISTED LASER DESORPTION IONIZATION

(75) Inventor: Nathalie Agar, Newton, MA (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 63 days.

(21) Appl. No.: 13/056,511

(22) PCT Filed: Jul. 24, 2009

(86) PCT No.: PCT/US2009/051740
§ 371 (c)(1),
(2), (4) Date: Jan. 28, 2011

(87) PCT Pub. No.: WO2010/014512
PCT Pub. Date: Feb. 4, 2010

(65) Prior Publication Data
US 2011/0192974 A1    Aug. 11, 2011

Related U.S. Application Data

(60) Provisional application No. 61/129,927, filed on Jul. 30, 2008.

(51) Int. Cl.
*H01J 49/00* (2006.01)
*H01J 49/04* (2006.01)
*G01N 1/32* (2006.01)

(52) U.S. Cl.
CPC ............ *H01J 49/0418* (2013.01); *G01N 1/32* (2013.01)

(58) Field of Classification Search
USPC ............... 250/281, 282, 283, 286, 287, 288
See application file for complete search history.

(56) References Cited

U.S. PATENT DOCUMENTS

| | | | |
|---|---|---|---|
| 6,177,266 B1 | 1/2001 | Krishnamurthy et al. | |
| 6,624,409 B1 | 9/2003 | Mordehai et al. | |
| 6,822,230 B2 | 11/2004 | Schleifer et al. | |
| 2003/0057106 A1 | 3/2003 | Shen et al. | |
| 2004/0119010 A1 | 6/2004 | Perryman et al. | |
| 2004/0119013 A1 | 6/2004 | Schleifer et al. | |
| 2004/0185448 A1 | 9/2004 | Lopez-Avila et al. | |
| 2005/0274885 A1* | 12/2005 | Brown et al. | 250/288 |
| 2006/0121599 A1* | 6/2006 | Reihs | 435/287.1 |
| 2006/0255262 A1* | 11/2006 | Sato et al. | 250/288 |
| 2007/0176093 A1* | 8/2007 | Kukla et al. | 250/288 |
| 2008/0050834 A1 | 2/2008 | Pamula et al. | |
| 2008/0128608 A1 | 6/2008 | Northen et al. | |

FOREIGN PATENT DOCUMENTS

WO   WO 2007/139989 A2   12/2007

OTHER PUBLICATIONS

International Search Report for PCT/US2009/051740 filed Jul. 24, 2009.
Written Opinion of the International Searching Authority for PCT/US2009/051740 filed Jul. 24, 2009.
International Preliminary Report on Patentability for PCT/US2009/051740 filed Jul. 24, 2009.
Agar, et al., "Matrix Solution Fixation: Histology-Compatible Tissue Preparation for MALDI Mass Spectrometry Imaging," *Anal. Chem.* 79:7416-7423 (2007).
Caprioli, et al., "Molecular Imaging of Biological Samples: Localization of Peptides and Proteins Using MALDI-TOF MS," *Anal. Chem.* 69:4751-4760 (1997).
Chaurand, et al., "Molecular imaging of thin mammalian tissue sections by mass spectrometry," *Curr. Opin. Biotechnol.* 17:431-436 (2006).
Gusev, et al., "Imaging of Thin-Layer Chromatograms Using Matrix-Assisted Laser Desorption/Ionization Mass Spectrometry," *Anal. Chem.* 67:4565-4570 (1995).
Harvey, "Matrix-assisted laser desorption/ionisation mass spectrometry of oligosaccharides and glycoconjugates," *J. Chromatog.* 720:429-446 (1996).
Karas, et al., "Laser Desorption Ionization of Proteins with Molecular Masses Exceeding 10,000 Daltons," *Anal. Chem.* 60:2299-2301 (1988).
Karas, et al., "Matrix-Assisted Ultraviolet Laser Desorption of Non-Volatile Compounds," *Int. J. Mass Spectrom. Ion Proc.* 78:53-68 (1987).
Rahman, et al., "Proteomic Patterns of Preinvasive Bronchial Lesions," *Am. J. Respir. Crit. Care Med.* 172:1556-1562 (2005).
Spengler, et al., "Gentle probe for tough molecules: matrix-assisted laser desorption mass spectrometry," *Analysis 20* :91-101 (1992).
Stoeckli, et al., "Imaging mass spectrometry: A new technology for the analysis of protein expression in mammalian tissues," *Nat. Med.* 7(4):493-496 (Apr. 2001).
Stoeckli, et al., "Automated Mass Spectrometry Imaging with a Matrix-Assisted Laser Desorption Ionization Time-of-Flight Instrument," *J. Am. Soc. Mass Spectrom.* 10:67-71 (1999).
Yanagisawa, et al., "Proteomic patterns of tumor subsets in non-small-cell lung cancer," *The Lancet* 362:433-439 (2003).
Zaluzec, et al., "Matrix-Assisted Laser Desorption Ionization Mass Spectrometry: Applications in Peptide and Protein Characterization," *Prot. Expr. Purif.* 6:109-123 (1995).

* cited by examiner

*Primary Examiner* — Nicole Ippolito
*Assistant Examiner* — Hanway Chang
(74) *Attorney, Agent, or Firm* — Quarles & Brady, LLP

(57) ABSTRACT

The present invention is directed, sample test plates that can be used in matrix assisted laser desorption ionization. These plates have an etched surface and a layer of MALDI matrix material. The invention also includes methods for making these sample test plates and to methods for using the plates in the MS imaging of cell and tissue samples.

21 Claims, No Drawings

PREPARATION OF TEST PLATES FOR MATRIX ASSISTED LASER DESORPTION IONIZATION

CROSS REFERENCE TO RELATED APPLICATIONS

The present application is US national stage of international application PCT/US2009/051740, which had an international filing date of Jul. 24, 2009 and claims the benefit of U.S. provisional application 61/129,927, filed on Jul. 30, 2008, the contents of which is hereby incorporated by reference in its entirety. The PCT application was published in English under PCT Article 21(2) on Feb. 4, 2010.

FIELD OF THE INVENTION

The present invention is concerned with methods of preparing sample test plates for MALDI mass spectrometry. It also includes the test plates themselves and methods of using these plates in obtaining mass spectral profiles of biological samples.

BACKGROUND

Matrix assisted laser desorption/ionization mass spectrometry (MALDI-MS) is typically performed by depositing a sample containing analyte on a solid support in the presence of a photon-absorbing matrix (usually a crystalline organic acid) (Karas, et al., *Anal. Chem.*, 60:2299-2301 (1988)). When exposed to pulses of laser light, the matrix transfers energy to molecules in the sample, thereby promoting their ionization and desorption. Because this technique is relatively gentle, large biological molecules such as proteins can be volatized without degradation or fragmentation (Karas et al. (1987) *Int. J. Mass. Spectrom. Ion Processes* 78:53 (1987); Spengler, et al., *Analysis* 20:91 (1992)). Once in the gas phase, the ions are transferred into a mass spectrometer and accelerated toward a detector by exposing them to an electric and/or a magnetic field. Time of flight (TOF), Ion Cyclotron Resonance (ICR), linear trap quadrupole, orbitrap based analysis can be used to determine the mass-to charge ratio of the molecules volatized from the sample.

Recently, attempts have been made to apply MALDI MS techniques diagnostically by identifying spectral profiles characteristic of disease states (Stoeckli, et al., *Nat. Med.* 7:493 (2001); Rahman et al., *Am. J. Respir. Crit. Care Med.* 172:1556 (2005); Yanagisawa, et al., *Lancet* 362:433 (2003); Chaurand, et al., *Curr. Opin. Biotechnol.* 17:431 (2006)). Using samples of cells and tissues, hundreds of peptide and protein peaks can be recorded in a mass spectrum produced from a single sample or from a single site on a sample (WO 2007/139989, Agar, et al., *Anal. Chem.* 79:7416-7423 (2007)). Moreover, scans of tissues may be performed in which hundreds of closely spaced MALDI MS spectra are taken in a grid pattern covering the entire sample (Gusev, et al. *Anal. Chem.* 67:4565 (1995); Stoeckli, et al., *J. Am. Soc. Mass Spectrom.* 10:67 (1999); Caprioli, et al., *Anal. Chem.* 69:4751 (1997)). Overall, MALDI Mass Spectrometry Imaging (MSI) has been shown to have the potential to rapidly detect diseased cells and reveal how they are distributed in tissues. This may be of enormous value in, for example, in making treatment decisions dependent upon the identity and aggressiveness of tumors, and the ability to predict a response to treatment.

Despite its promise, MS imaging has not yet been used clinically as a diagnostic tool to a significant degree. In part, this is because inconsistencies in the size and distribution of matrix particles on support surfaces creates site to site variability in the amount of energy transferred and, consequently, in molecule desorption. As a result, spectra do not accurately reflect the distribution of molecules in tissues and are only poorly reproduced from one analysis to the next. Thus, better methods for preparing matrix surfaces for MALDI MS are critical to the advance of this technology.

SUMMARY OF THE INVENTION

The present invention is directed to techniques for making homogeneous MALDI matrix surfaces and is based, in part, on the etching of solid supports prior to matrix deposition. This creates a more uniform distribution of matrix crystals and, ultimately, scans that better reflect the molecules present in samples and that are more reproducible.

In its first aspect, the invention is directed to a method of preparing a sample test plate that can be used in carrying out MALDI MS. The term "sample test plate" refers to a wafer, slide, or other object on which samples such as cells and tissues can be mounted for MS analysis. The sample test plate is made up of a solid support (such as stainless steel, silicon, plastic, teflon, or glass) with a flat surface that is coated with a dry layer of MALDI matrix material. The term "MALDI matrix material" refers to chemical compounds capable of crystallizing on the surface of the support and that transfer energy from incident laser light to sample molecules either mounted on it or co-deposited during matrix crystallization. Any MALDI matrix materials known in the art may be used for preparing plates including: 3-hydroxypicolinic acid (3-hydroxy-2-pyridinecarboxylic acid), nicotinic acid-N-oxide, 2'-6'-dihydroxyacetophenone, 2,5-dihydroxy-benzoic acid), α-cyano-4-hydroxycinnamic acid, (4-hydroxy-3-methoxycinnamic acid), and 3,5-dimethoxy-4-hydroxy-cinnamic acid (sinapinic acid).

The test plates are prepared by first etching the surface of the solid support to provide sites for matrix crystal nucleation. A layer of MALDI matrix solution or suspension (i.e., MALDI matrix material that has been dissolved or suspended in a solvent) is then applied to the etched surface and matrix particles are allowed to crystallize while concurrently, or subsequently, removing solvent to produce a dry layer of matrix. MALDI matrices may be applied to surfaces by solvent evaporation deposition, spin coating, spraying, electrospraying, blade deposition, or chemical printing. When dried, the matrix layer should be no more than 5 um thick and provide homogenous coverage such that no more than a 1 um by 1 um area of surface is devoid of matrix. In addition, the matrix crystals should have an average size of between 1 um and 100 um.

Preferably, plates are etched by photolithography to produce an even distribution of abrasions that serve as nucleation sites for crystallization. The term "even distribution" means that the number of etch abrasions in each 10 um by 10 um area of surface varies by 20% or less and, preferably, by 10, 5 or 1% or less. Solid supports may be made of a conductive, nonconductive or semiconductive material and may be coated with an organic or inorganic compound that alters conductivity. For example, the support may be made of stainless steel, silicon, glass, plastic teflon etc. and, optionally, coated with materials such as silicon, indium tin oxide, aromatic hydrocarbons or polyacetylenes. Specific examples of organic coatings include pentacene, anthracene rubrene poly(3-hexylthiophene), and poly(p-phenylene vinylene).

The method described above may include the formation of an organic semiconductor. The term "organic semiconductor" as used herein refers to any organic material that, either alone or when deposited on the surface of a solid support, has semiconductor properties, i.e., has an electrical conductivity between that of typical metals such as copper and that of insulating compounds. Typically, organic semiconductors comprise aromatic hydrocarbons or polyacetylenes and include compounds such as pentacene, anthracene rubrene poly(3-hexylthiophene), and poly(p-phenylene vinylene). Thus, the invention encompasses a method of preparing a sample test plate by: a) etching the surface of a solid support to provide sites for crystal nucleation; b) crystallizing an organic compound on to the etched surface so that the surface and the crystallized organic compound together form an organic semiconductor; c) applying a layer of MALDI matrix solution or suspension to the organic semiconductor; d) allowing matrix particles to crystallize on the surface; and e) concurrently or subsequently removing solvent to produce a dry layer of MALDI matrix material. As discussed above, the preferred method of etching plates is by photolithography to produce an even distribution of nucleation sites. MALDI matrix materials include 3-hydroxypicolinic acid (3-hydroxy-2-pyridinecarboxylic acid), nicotinic acid-N-oxide, 2'-6'-dihydroxyacetophenone, 2,5-dihydroxybenzoic acid), α-cyano-4-hydroxycinnamic acid, (4-hydroxy-3-methoxycinnamic acid), and 3,5-dimethoxy-4-hydroxy-cinnamic acid and may be applied by any of the techniques described above. The dry matrix layer formed should be no more than 5 um in thickness. It should provide homogeneous coverage of the surface (i.e., no more than a 1 um by 1 um area should be devoid of matrix) and should, preferably, have crystals with an average size of between 1 um and 100 um.

In another variation of the above methods, an organosilicon may be applied to the surface of plates to serve as an organic semiconductor. As used herein, the term "organosilicon" refers to any organic compound having a carbon-silicon bond. In some cases, the organosilicon may itself serve as the MALDI matrix and form a layer that transfers energy from incident laser light to cell or tissue samples mounted on its surface. Alternatively, the organosilicon may be deposited on the support surface and then overlaid with a MALDI matrix layer. In this aspect, the method entails: a) etching the surface of a solid support to provide sites for crystal nucleation; b) applying an organosilicon that is dissolved or suspended in a solvent to the etched surface; and c) removing solvent to produce a dry layer of organosilicon. Optionally, the method may further include the steps of: d) applying a layer of MALDI matrix solution or suspension to the dry layer of organosilicon; and e) allowing matrix particles to crystallize on to the organosilicon surface while concurrently, or subsequently, removing solvent from the solution or suspension to produce a dry layer of MALDI matrix material. The organosilicon and/or the MALDI matrix material may comprise a compound selected from the group consisting of: 3-hydroxypicolinic acid (3-hydroxy-2-pyridinecarboxylic acid), nicotinic acid-N-oxide, 2'-6'-dihydroxyaceto-phenone, 2,5-dihydroxybenzoic acid), α-cyano-4-hydroxycinnamic acid, (4-hydroxy-3-methoxycinnamic acid), and 3,5-dimethoxy-4-hydroxy-cinnamic acid. Solid supports can be made of conductive, nonconductive or semiconductive materials such as stainless steel, silicon or glass. Organosilicon and/or MALDI matrix solutions or suspensions may be applied to surfaces by solvent evaporation deposition, spin coating, spraying, blade deposition, or chemical printing. Each layer should, preferably, be no more than 5 um thick, provide homogenous coverage of the solid support surface and comprise crystals with an average size of between 1 um and 100 um.

In another aspect, the invention is directed to a test plate that can be used in carrying out MALDI MS techniques which comprises a) a solid support with a flat surface that has been etched to provide sites for crystal nucleation; and b) a dry layer of MALDI matrix material covering the surface of the solid support. The layer of MALDI matrix material should be no more than 5 um in thickness, provide homogenous coverage such that no more than a 1 um by 1 um of surface area is devoid of matrix and have crystals with an average size of between 1 um and 100 um. The sample test plate may optionally include organic compounds (e.g., aromatic hydrocarbons or a polyacetylenes) that have been deposited on the surface of the solid support such that the surface and the organic compound together form an organic semiconductor. Examples of specific organic compounds that may be used in this manner include pentacene, anthracene rubrene poly(3-hexylthiophene), and poly(p-phenylene vinylene). In addition, the MALDI matrix material may be an organosilicon or the sample test plate may include an organosilicon layer between the surface of the solid support and the dry layer of MALDI matrix material.

In another aspect, the invention is directed to a method of diagnostically analyzing a cell or tissue sample by applying the sample to one of the test sample plates described above and exposing the sample to laser light at a wavelength where the MALDI matrix material absorbs and transfers energy to molecules in the sample. The vaporized compounds thus created are then analyzed by MS to obtain a spectral profile of the sample. Types of MS that may be used include, but are not limited to: time of flight MS, linear trap quadrupole MS, Fourier transform (or ICR) MS, orbitrap MS etc. By comparing the profile obtained in this manner with profiles from tissue and cell samples with known biological characteristics, a determination can be made concerning the characteristics of the sample, e.g., whether it is cancerous or non-cancerous, rapidly growing or slow growing etc.

DETAILED DESCRIPTION OF THE INVENTION

The present invention is directed to the preparation of plates that can be used for the mass spectrometry imaging of cells and tissues. The main problem with such analyses is that variability in MALDI matrix surfaces distort spectra and create poor reproducibility. This variability is primarily caused by the relatively heterogeneous crystallization of the matrix which, in turn, causes different peak intensities for a given molecule at a given concentration. In the imaging of biological tissue using MALDI, the phenomenon becomes even more problematic in that the application is typically designed to represent the relative distributions of molecules throughout the entire tissue specimen.

Thus, the overall objective of the present invention was to make surfaces used in MALDI more homogeneous in terms of crystal distribution, surface coverage, matrix thickness, and crystal size and shape. This has been accomplished by etching the surface of the solid supports used in MS to provide a uniform pattern of abrasions that serve as nucleation sites during crystallization. The conductivity of surfaces, another important factor in variability, is determined by initial conductivity of the solid support and is adjusted by the deposition of organic and inorganic compounds. In one preferred embodiment, the MALDI matrix forms an organic semiconductor when crystallized on to a solid support or the MALDI matrix is layered over an organic semiconductor layer formed by the deposition of selected organic compounds on the surface of the solid support. Alternatively, organic compounds may be covalently bound to a semiconductive material such as silicon and deposited on solid support surfaces prior to the crystallization of MALDI matrix particles.

Photolithography

Photolithography etching techniques are well known in the art and have been extensively used in the making of semiconductor chips. Most typically, this process uses light to transfer a geometric pattern from a photomask to a light sensitive material (photoresist). A series of chemical treatments are then used to complete the etching process. For example, plates may be coated with a thin (0.5-2.5 μm thick) layer of photoresist (e.g., poly(vinyl cinnamate), Novolak polymers or diazonaphthoquinone) and then heated to drive off solvent. The dried photoresist is then exposed to intense (usually UV) light which alters the stability of the photoresist and allows it to be removed upon exposure to developer (e.g., sodium hydroxide or tetramethylammonium hydroxide). After heating to stabilize the remaining photoresist, the plate is chemically etched to remove the uppermost layer of substrate on those areas of the plate not protected by photoresist. Finally, after etching has been completed, all of the photoresist is removed and the plate is washed and dried. Geometric etch patterns may be created on the plates by using a photomask during light exposure system or by using a light projection system. Many variations of this basic procedure are known in the art and are compatible with the etching of the test sample plates.

MALDI Matrices and Surfaces

A wide variety of MALDI matrix materials have been described in the art, are commercially available and can be used in conjunction with the present invention (see e.g., Sigma-Aldrich *Analytix vol.* 6 (2001), incorporated by reference herein in its entirety). The matrix may be deposited on plates using a variety of techniques such as solvent evaporation deposition, spin coating, spraying, electrospraying, blade deposition, and chemical printing, with the most preferred method being spin coating. The matrix layer should be no greater than about 5 um in thickness and uniformly cover support surfaces. Crystal characteristics can be controlled by manipulating crystallization kinetics, e.g., by varying the concentration of matrix material in solutions or suspensions, changing solvents and changing the conditions (e.g., temperature and pressure) under which crystallization is performed. Preferably matrix crystals should have a diameter of between 1 um and 100 um.

Use of Plates for Analysis of Biological Tissue

Detailed descriptions of MALDI MS and its applications may be found in review articles by Zaluzec, et al. (*Prot. Expression Pur* 6:109-123 (1995)) and Harvey (*J. Chromatog.* 720:429-4446 (1996), incorporated by reference herein in their entirety). This technique has been successfully applied both to the analysis of cells (see U.S. Pat. No. 6,177,266, incorporated by reference herein in its entirety) and tissues (see Agar, et al., *Anal Chem.* 79:7416-7423 (2007); WO 2007/139989, incorporated by reference herein in their entirety). For example, in the case of tissues, a thin section of tissue may be applied directly to a matrix-coated sample support and treated either before or after with a fixative or frozen. Types of MS that may be carried out include time of flight MS, linear trap quadrupole MS, Fourier transform (or ICR) MS, orbitrap MS.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of preparing a sample test plate suitable for matrix assisted laser desorption ionization (MALDI) mass spectrometry (MS) of a cell or a tissue sample and comprising a solid support that is coated on its surface with a dry layer of MALDI matrix material, said method comprising:
    a) etching the surface of said solid support using a photolithography etching technique to provide sites for crystal nucleation;
    b) applying a layer of MALDI matrix solution or suspension to substantially the entire surface of the solid support;
    c) allowing matrix particles to crystallize on said surface; and
    d) either concurrently or subsequently, removing solvent from said solution or suspension to produce a dry layer of MALDI matrix material providing a homogenous coverage of the solid support, wherein the dry layer of MALDI matrix material is substantially free of cells or tissue samples.

2. The method of claim 1, wherein said MALDI matrix material is selected from the group consisting of: 3-hydroxypicolinic acid (3-hydroxy-2-pyridinecarboxylic acid), nicotinic acid-N-oxide, 2'-6'-dihydroxyacetophenone, 2,5-dihydroxybenzoic acid, a-cyano-4-hydroxycinnamic acid, 4-hydroxy-3-methoxycinnamic acid, and 3,5-dimethoxy-4-hydroxy-cinnamic acid (sinapinic acid).

3. The method of claim 1, wherein said solid support has been coated with indium tin oxide, an aromatic hydrocarbon or a polyacetylene.

4. The method of claim 1, wherein said dry layer of matrix material is no more than 5 um in thickness and provides homogenous coverage such that no more than 1 um by 1 um of surface area is devoid of matrix.

5. The method of claim 1, wherein said dry layer of MALDI matrix material comprises crystals with an average size of between 1 um and 100 um.

6. The method of claim 1, further comprising, prior to step b), crystallizing an organic compound on to the etched surface prepared in step a) so that the surface and the crystallized organic compound together form an organic semiconductor.

7. The method of claim 6, wherein said MALDI matrix material is selected from the group consisting of: 3-hydroxypicolinic acid (3-hydroxy-2-pyridinecarboxylic acid), nicotinic acid-N-oxide, 2'-6'-dihydroxyacetophenone, 2,5-dihydroxybenzoic acid, a-cyano-4-ydroxycinnamic acid, 4-hydroxy-3-methoxycinnamic acid, and 3,5-dimethoxy-4-hydroxy-cinnamic acid (sinapinic acid).

8. The method of claim 6, wherein said solid support is made of a conductive material, or a semiconductive material.

9. The method of claim 6, wherein said organic compound is an aromatic hydrocarbon or a polyacetylene.

10. The method of claim 6, wherein said organic compound is selected from the group consisting of: pentacene, anthracene rubrene poly(3-hexylthiophene), and poly(p-phenylene vinylene).

11. The method of claim 6, wherein said dry layer of matrix material is no more than 5 um in thickness and provides homogenous coverage such that no more than 1 um by 1 um of surface area is devoid of matrix.

12. The method of claim 6, wherein said dry layer of MALDI matrix material comprises crystals with an average size of between 1 um and 100 um.

13. A sample test plate that can be used in carrying out MALDI MS of a cell or a tissue sample, comprising:
   a) a solid support with a flat surface that has been etched using a photolithography etching technique to provide sites for crystal nucleation; and
   b) a dry layer of MALDI matrix material covering the surface of said solid support, wherein said dry layer:
      i) is no more than 5 um thick;
      ii) provides homogenous coverage such that no more than a 1 um by 1 um area of surface is devoid of matrix;
      iii) comprises crystals with an average size of between 1 um and 100 um; and
      iv) is substantially free of cells or tissue samples.

14. The sample test plate of claim 13, further comprising a dry layer of organic compounds between said surface of said solid support and said layer of MALDI matrix material, wherein said surface and said organic compounds together form organic semiconductors.

15. The sample test plate of claim 14, wherein said organic compounds are aromatic hydrocarbons or polyacetylenes.

16. The sample test plate of claim 14, wherein said organic compounds are selected from the group consisting of: pentacene, anthracene rubrene poly(3-hexylthiophene), and poly(p-phenylene vinylene).

17. The sample test plate of claim 13, wherein said MALDI matrix material is selected from the group consisting of: 3-hydroxypicolinic acid (3-hydroxy-2-pyridinecarboxylic acid), nicotinic acid-N-oxide, 2'-6'-dihydroxyacetophenone, 2,5-dihydroxybenzoic acid, a-cyano-4-hydroxycinnamic acid, 4-hydroxy-3-methoxycinnamic acid, and 3,5-dimethoxy-4-hydroxy-cinnamic acid.

18. The sample test plate of claim 13, wherein said MALDI matrix material comprises organosilicons.

19. The sample test plate of claim 13, further comprising organosilicons between the surface of said solid support and said dry layer of MALDI matrix material.

20. The sample test plate of claim 19, wherein at least one of said organosilicon and said MALDI matrix material, comprises a compound selected from the group consisting of: 3-hydroxypicolinic acid (3-hydroxy-2-pyridinecarboxylic acid), nicotinic acid-N-oxide, 2'-6'-dihydroxyacetophenone, 2,5-dihydroxybenzoic acid, acyano-4-hydroxycinnamic acid, 4-hydroxy-3-methoxycinnamic acid, and 3,5-dimethoxy-4-hydroxy-cinnamic acid (sinapinic acid).

21. A method of preparing a sample test plate suitable for matrix assisted laser desorption ionization (MALDI) mass spectrometry (MS) of a cell or a tissue sample and comprising a solid support that is coated on its surface with a dry layer of MALDI matrix material, the method comprising:
   a) etching the surface of the solid support using a photolithography etching technique to provide sites for crystal nucleation;
   b) applying a layer of MALDI matrix solution or suspension to the etched surface prepared in step a);
   c) allowing matrix particles to crystallize on the etched surface;
   d) either concurrently with step c) or subsequent to step c), removing solvent from the solution or suspension to produce a dry layer of MALDI matrix material providing a homogeneous coverage of the solid support; and
   e) directly applying the cell or the tissue sample to the dry layer of MALDI matrix material.

* * * * *